(12) United States Patent
Lee et al.

(10) Patent No.: US 11,407,739 B2
(45) Date of Patent: Aug. 9, 2022

(54) COMPOUND AND OPTICAL FILTER AND IMAGE SENSOR AND CAMERA MODULE AND ELECTRONIC DEVICE

(71) Applicant: Samsung Electronics Co., Ltd., Suwon-si (KR)

(72) Inventors: Yong Joo Lee, Suwon-si (KR); Changki Kim, Suwon-si (KR); Jae Jun Lee, Suwon-si (KR); Mi Jeong Kim, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 181 days.

(21) Appl. No.: 16/673,385

(22) Filed: Nov. 4, 2019

(65) Prior Publication Data
US 2020/0331892 A1 Oct. 22, 2020

(30) Foreign Application Priority Data
Apr. 18, 2019 (KR) ........................ 10-2019-0045761

(51) Int. Cl.
| | | |
|---|---|---|
| C07D 403/06 | (2006.01) | |
| H01L 51/00 | (2006.01) | |
| H01L 27/146 | (2006.01) | |
| C07D 209/60 | (2006.01) | |
| H04N 5/33 | (2006.01) | |
| G02F 1/1335 | (2006.01) | |

(52) U.S. Cl.
CPC ......... *C07D 403/06* (2013.01); *C07D 209/60* (2013.01); *H01L 27/14621* (2013.01); *H01L 27/14645* (2013.01); *H01L 27/14649* (2013.01); *H01L 51/0072* (2013.01); *G02F 1/133509* (2013.01); *H04N 5/33* (2013.01)

(58) Field of Classification Search
CPC ............................. C07D 403/06; C07D 209/60
See application file for complete search history.

(56) References Cited

U.S. PATENT DOCUMENTS

| | | | |
|---|---|---|---|
| 4,876,181 | A | 10/1989 | Proehl et al. |
| 5,714,307 | A | 2/1998 | Harada et al. |
| 5,783,377 | A | 7/1998 | Mee et al. |
| 5,853,969 | A | 12/1998 | Harada et al. |
| 6,342,335 | B1 | 1/2002 | Fujita et al. |
| 6,716,509 | B2 | 4/2004 | Yeh et al. |
| 6,775,059 | B2 | 8/2004 | Kuwabara |
| RE39,105 | E | 5/2006 | Fujita et al. |
| 2011/0224334 | A1* | 9/2011 | Maeda ................ C09B 23/0041 524/89 |

FOREIGN PATENT DOCUMENTS

| | | | |
|---|---|---|---|
| JP | 04359244 | * | 12/1992 |
| JP | H08295821 | A | 11/1996 |
| JP | 2614862 | B2 | 5/1997 |
| JP | H10152620 | A | 6/1998 |
| JP | 2000265076 | * | 9/2000 |
| JP | 2002338822 | A | 11/2002 |
| JP | 2004093758 | * | 3/2004 |
| JP | 3517210 | B2 | 4/2004 |
| JP | 3606165 | B2 | 1/2005 |
| JP | 3616173 | B2 | 2/2005 |
| JP | 2015183134 | A | 10/2015 |

OTHER PUBLICATIONS

Dorwald; "Side Reactions in Organic Synthesis a Guide to Successful Synthesis Design", Wiley-VCH, 2005, Preface and Chapter 1, 32 pages. (Year: 2005).*
Mojzych; "Synthesis of Cyanine Dyes", Top Heterocycl Chem, 2008, 14, 1-9. (Year: 2008).*
Benson; Journal of Chemical and Engineering Data, 1977, 22, 379-383. (Year: 1977).*
J. L. Bricks et al., 'Molecular design of near infrared polymethine dyes: A review' *Dyes and Pigments*, vol. 121, 2015, pp. 238-255.
Gaussian 16, Expanding the limits of computational chemistry (2016), retrieved at http://gaussian.com/citation/ on Mar. 30, 2020.
Lepkowicz et. al., "Excited-state absorption dynamics in polymthine dyes detected by polarization-resolved pump-probe measurements," Chemical Physics, vol. 286, No. 2-3, pp. 277-291 (Jan. 15, 2003).
Lepkowicz et. al., "Absorption anisotropy studies of polymethine dyes," Chemical Physics, vol. 306, No. 1-3, pp. 171-183 (Nov. 15, 2004).
Pazenok et. al. "Indo- and Benzindocyanine Dyes wit Flourine-containing Substituents," Chemistry of Heterocyclic Compounds, vol. 19, No. 11, pp. 1182-1187 (Nov. 1983).

* cited by examiner

*Primary Examiner* — Daniel R Carcanague
(74) *Attorney, Agent, or Firm* — Harness, Dickey & Pierce, P.L.C.

(57) ABSTRACT

Disclosed are a compound represented by Chemical Formula 1, an optical filter, an image sensor, a camera module, and an electronic device.

[Chemical Formula 1]

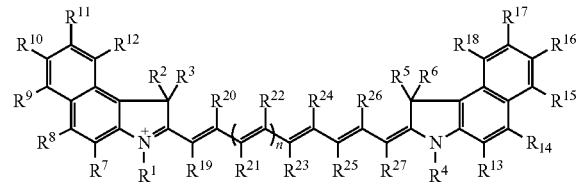

In Chemical Formula 1, $R^1$ to $R^{27}$ and n are the same as defined in the detailed description.

20 Claims, 4 Drawing Sheets

COMPOUND AND OPTICAL FILTER AND IMAGE SENSOR AND CAMERA MODULE AND ELECTRONIC DEVICE

CROSS-REFERENCE TO RELATED APPLICATION

This application claims priority to and the benefit of Korean Patent Application No. 10-2019-0045761 filed in the Korean Intellectual Property Office on Apr. 18, 2019, the entire contents of which are incorporated herein by reference.

BACKGROUND

1. Field

A compound, an optical filter, an image sensor, a camera module, and an electronic device are disclosed.

2. Description of the Related Art

Recently, an electronic device including an image sensor that stores an image as an electrical signal, such as a cell phone, a digital camera, a camcorder, and a camera, has been widely used. This electronic device may include an optical filter in order to reduce or prevent generation of an optical distortion by light in the other regions than a visible region.

SUMMARY

An embodiment provides a compound capable of effectively absorbing light in a near-infrared wavelength region.

Another embodiment provides an optical filter including the compound.

Another embodiment provides an image sensor including the optical filter.

Another embodiment provides a camera module including the optical filter or the image sensor.

Another embodiment provides an electronic device including the optical filter, the image sensor or the camera module.

According to an embodiment, a compound represented by Chemical Formula 1 is provided.

In Chemical Formula 1, $R^1$ to $R^6$ are each independently hydrogen or a C1 to C5 alkyl group, $R^7$ to $R^{27}$ are each independently hydrogen, a substituted or unsubstituted C1 to C20 alkyl group, a substituted or unsubstituted C3 to C20 cycloalkyl group, a substituted or unsubstituted C6 to C20 aryl group, a substituted or unsubstituted C3 to C20 heterocyclic group, a substituted or unsubstituted C1 to C20 alkoxy group, —$NR^aR^b$, —$NHCOR^c$, —$OCOR^d$, a hydroxy group, a halogen, a cyano group, or a combination thereof, and $R^7$ to $R^{27}$ are each independently present or two of these are linked with each other to form a ring, at least one of $R^7$ to $R^{18}$ is a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof, $R^a$ to $R^d$ are each independently hydrogen, a substituted or unsubstituted C1 to C20 alkyl group, a substituted or unsubstituted C6 to C20 aryl group, or a combination thereof, and n is 1 or 2.

In some embodiments, a light absorption spectrum of the compound may have a maximum absorption wavelength in a wavelength of about 890 nm to about 990 nm.

In some embodiments, a maximum absorption wavelength of the compound represented by Chemical Formula 1 may be shifted into a long wavelength by greater than or equal to about 5 nm compared with a maximum absorption wavelength of a comparative compound in which each of $R^7$ to $R^{18}$ of Chemical Formula 1 is hydrogen.

In some embodiments, at least one of $R^7$ to $R^{12}$ and at least one of $R^{13}$ to $R^{18}$ may each independently be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof. And $R^a$ to $R^d$ may each independently be hydrogen, a substituted or unsubstituted C1 to C20 alkyl group, a substituted or unsubstituted C6 to C20 aryl group, or a combination thereof.

In some embodiments, at least one of $R^8$, $R^{10}$, $R^{14}$, and $R^{16}$ may be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof. And $R^a$ to $R^d$ may each independently be hydrogen, a substituted or unsubstituted C1 to C20 alkyl group, a substituted or unsubstituted C6 to C20 aryl group, or a combination thereof.

[Chemicl Formula 1]

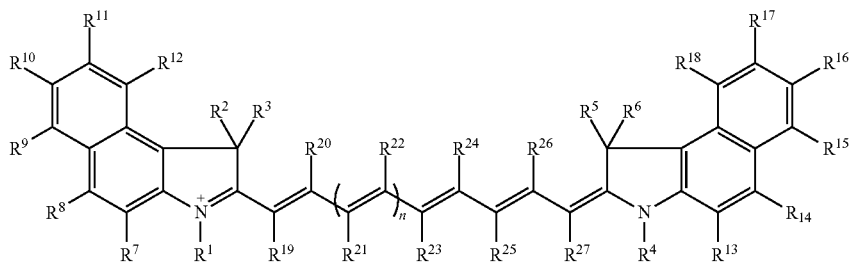

In some embodiments, $R^8$ and $R^{14}$ may each independently be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof. And $R^a$ to $R^d$ may each independently be hydrogen, a substituted or unsubstituted C1 to C20 alkyl group, a substituted or unsubstituted C6 to C20 aryl group, or a combination thereof.

In some embodiments, $R^{10}$ and $R^{16}$ may each independently be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof. And $R^a$ to $R^d$ may each independently be hydrogen, a substituted or unsubstituted C1 to C20 alkyl group, a substituted or unsubstituted C6 to C20 aryl group, or a combination thereof.

In some embodiments, $R^1$ to $R^6$ may each independently be a methyl group, an ethyl group, or a propyl group.

In some embodiments, the compound may be represented by Chemical Formula 1A or 1B.

at least one of $R^7$ to $R^{18}$ may be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof, $R^a$ to $R^j$ may each independently be hydrogen, a substituted or unsubstituted C1 to C20 alkyl group, a substituted or unsubstituted C6 to C20 aryl group, or a combination thereof, and n may be 1 or 2.

In some embodiments, at least one of $R^7$ to $R^{12}$ and at least one of $R^{13}$ to $R^{18}$ may each independently be a substituted

[Chemical Formula 1A]

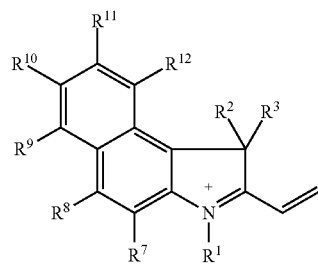 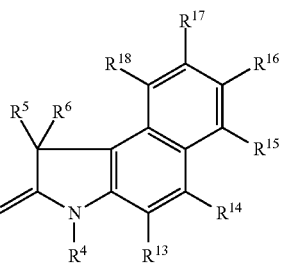

[Chemical Formula 1B]

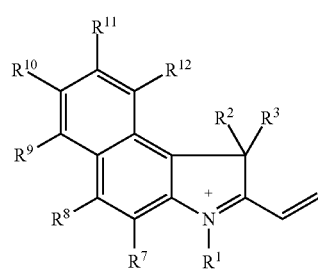 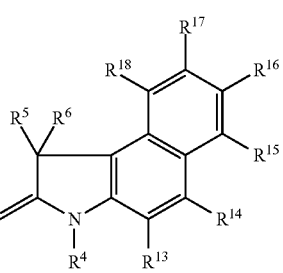

In Chemical Formula 1A or 1B, $R^1$ to $R^6$ may each independently be hydrogen or a C1 to C5 alkyl group, $R^7$ to $R^{18}$ and $R^{23}$ may each independently be hydrogen, a substituted or unsubstituted C1 to C20 alkyl group, a substituted or unsubstituted C3 to C20 cycloalkyl group, a substituted or unsubstituted C6 to C20 aryl group, a substituted or unsubstituted C3 to C20 heterocyclic group, a substituted or unsubstituted C1 to C20 alkoxy group, —$NR^aR^b$, —$NHCOR^c$, —$OCOR^d$, a hydroxy group, a halogen, a cyano group, or a combination thereof, or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof. And $R^a$ to $R^d$ may each independently be hydrogen, a substituted or unsubstituted C1 to C20 alkyl group, a substituted or unsubstituted C6 to C20 aryl group, or a combination thereof.

In some embodiments, the compound may be represented by one of Chemical Formulae 1A-1, 1A-2, 1B-1, and 1B-2.

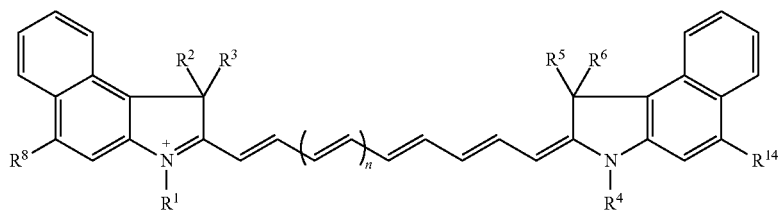

[Chemical Formula 1A-1]

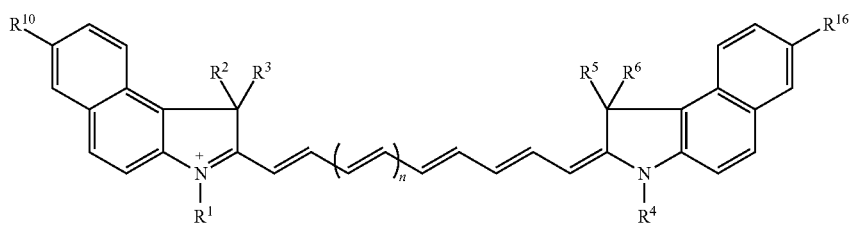

[Chemical Formula 1A-2]

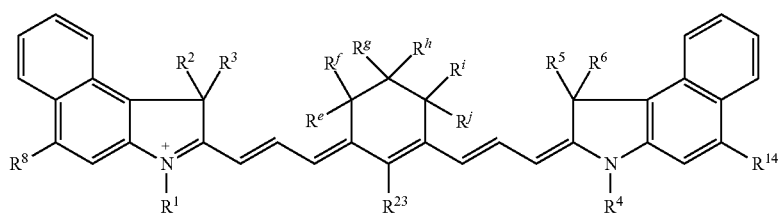

[Chemical Formula 1B-1]

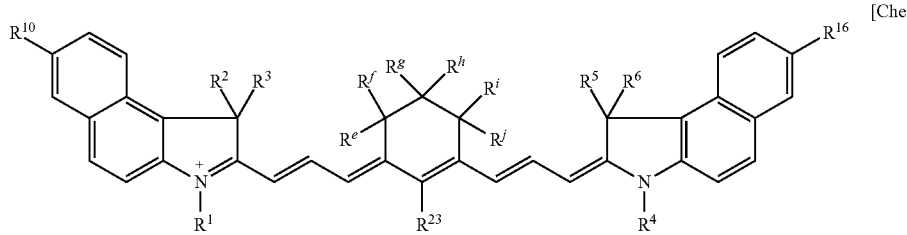

[Chemical Formula 1B-2]

In Chemical Formulae 1A-1, 1A-2, 1B-1, and 1B-2, $R^1$ to $R^6$ are each independently hydrogen or a C1 to C5 alkyl group, $R^8$, $R^{10}$, $R^{14}$, and $R^{16}$ may each independently be a substituted or unsubstituted C1 to C20 alkyl group, a substituted or unsubstituted C3 to C20 cycloalkyl group, a substituted or unsubstituted C6 to C20 aryl group, a substituted or unsubstituted C3 to C20 heterocyclic group, a substituted or unsubstituted C1 to C20 alkoxy group, —$NR^aR^b$, —$NHCOR^c$, —$OCOR^d$, a hydroxy group, a halogen, a cyano group, or a combination thereof, $R^e$ to $R^j$ may each independently be hydrogen, a substituted or unsubstituted C1 to C20 alkyl group, a substituted or unsubstituted C6 to C20 aryl group, or a combination thereof, and n may be 1 or 2.

According to another embodiment, an optical filter may include the compound or a cured product thereof.

According to another embodiment, an image sensor may include a semiconductor substrate and an optical filter on the semiconductor substrate. The optical filter may be configured to absorb at least a portion of light in a near-infrared wavelength region. The optical filter may include the compound or a cured product thereof.

In some embodiments, the semiconductor substrate may include a plurality of photodiodes.

In some embodiments, the image sensor may further include a color filter on the semiconductor substrate and on or under the optical filter.

In some embodiments, the image sensor may further include a dual band-pass filter configured to transmit all the visible wavelength region and a portion of the near-infrared wavelength region.

According to another embodiment, a camera module including the optical filter or the image sensor is provided.

According to another embodiment, an electronic device including the optical filter, the image sensor or the camera module is provided.

The compound may be effectively applied to a near-infrared absorption filter and an image sensor having a near-infrared absorption filter by effectively absorbing light of a desired (and/or alternatively predetermined) wavelength belonging to a near-infrared wavelength region.

DETAILED DESCRIPTION

Figure 1:
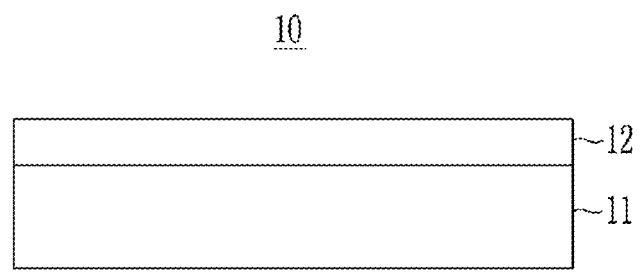
FIG. 1 is a cross-sectional view showing an optical filter according to an embodiment.

Example embodiments will hereinafter be described in detail, and may be easily performed by a person skilled in the related art. However, this disclosure may be embodied in many different forms and is not to be construed as limited to the exemplary embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, when a definition is not otherwise provided, "substituted" refers to the case where hydrogen of a compound is replaced by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" refers to inclusion of one to four heteroatoms selected from N, O, S, Se, Te, Si, and P.

As used herein, when a definition is not otherwise provided, "aryl group" refers to a group including at least one hydrocarbon aromatic moiety, and includes hydrocarbon aromatic moieties linked by a single bond and hydrocarbon aromatic moieties fused directly or indirectly to provide a non-aromatic fused ring. The aryl group may include a monocyclic, polycyclic or fused polycyclic (e.g., rings sharing adjacent pairs of carbon atoms) functional group.

As used herein, when a definition is not otherwise provided, "heterocyclic group" includes a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

As used herein, "combination" includes mixing, copolymerization, or two or more stack structures.

Hereinafter, a compound according to an embodiment is described.

The compound according to an embodiment is represented by Chemical Formula 1.

[Chemicl Formula 1]

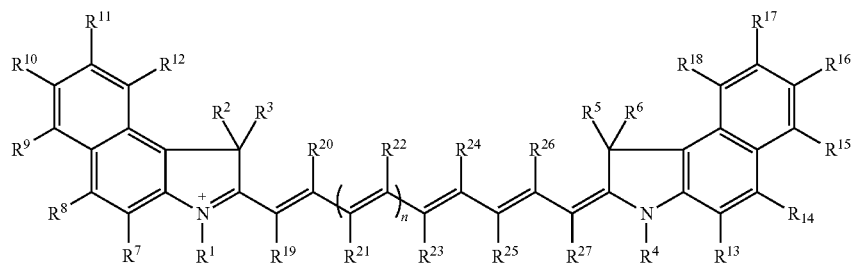

In Chemical Formula 1, $R^1$ to $R^6$ are each independently hydrogen or a C1 to C5 alkyl group, $R^7$ to $R^{27}$ are each independently hydrogen, a substituted or unsubstituted C1 to C20 alkyl group, a substituted or unsubstituted C3 to C20 cycloalkyl group, a substituted or unsubstituted C6 to C20 aryl group, a substituted or unsubstituted C3 to C20 heterocyclic group, a substituted or unsubstituted C1 to C20 alkoxy group, —$NR^aR^b$, —$NHCOR^c$, —$OCOR^d$, a hydroxy group, a halogen, a cyano group, or a combination thereof, wherein $R^a$ to $R^d$ are each independently hydrogen, a substituted or unsubstituted C1 to C20 alkyl group, a substituted or unsubstituted C6 to C20 aryl group, or a combination thereof, $R^7$ to $R^{27}$ are each independently present or two of these are linked with each other to form a ring, at least one of $R^7$ to $R^{18}$ is an electron donating group, and n is 1 or 2.

The compound is a light absorbing material configured to selectively absorb at least a portion of light of a near-infrared wavelength region, and may be for example a light absorbing material configured to absorb light in a wavelength region of greater than or equal to about 850 nm, greater than or equal to about 870 nm, greater than or equal to about 890 nm, greater than or equal to about 900 nm, greater than or equal to about 910 nm, or greater than or equal to about 920 nm.

For example, a light absorption spectrum of the compound may have a maximum absorption wavelength (λmax) in a wavelength region of about 850 nm to about 1100 nm, for example about 870 nm to about 1050 nm, about 880 nm to about 1000 nm, about 890 nm to about 990 nm, about 900 nm to about 990 nm, about 910 nm to about 990 nm, or about 920 nm to about 990 nm.

For example, a light absorption rate (absorbance or absorptance) of the compound at the maximum absorption wavelength (λmax) may be greater than or equal to about 50% and less than or equal to about 100%, for example greater than or equal to about 60%, greater than or equal to about 70%, greater than or equal to about 80% or greater than or equal to about 85%.

For example, the compound may not be configured to substantially absorb light in a visible wavelength region and may have, for example about a light absorption rate in a wavelength region of about 400 nm to about 700 nm of less than or equal to about 10%, less than or equal to about 7%, less than or equal to about 5%, less than or equal to about 3%, less than or equal to about 2%, less than or equal to about 1%, less than or equal to about 0.5%, or about 0%.

The compound may have a benzoindole moiety substituted with an electron donating group, and thereby may be configured to absorb light in a further long wavelength in a near-infrared wavelength region. For example, a maximum absorption wavelength ($\lambda_{max}$) of the compound may be shifted into a long wavelength by greater than or equal to about 5 nm, greater than or equal to about 7 nm, greater than or equal to about 10 nm, greater than or equal to about 15 nm, greater than or equal to about 20 nm, or greater than or equal to about 5 nm to about 50 nm, about 7 nm to about 50 nm, about 10 nm to about 50 nm, about 15 nm to about 50 nm, or about 20 nm to about 50 nm, compared with a maximum absorption wavelength ($\lambda_{max}$) of a comparative compound having unsubstituted benzoindole moiety ($R^7$ to $R^{18}$ are each hydrogen) instead of the benzoindole moiety substituted with an electron donating group.

For example, at least one of $R^1$ to $R^6$ may be a C1 to C5 alkyl group, for example a methyl group, an ethyl group, or a propyl group.

For example, each of $R^1$ to $R^6$ may be a C1 to C5 alkyl group and may be each independently a methyl group, an ethyl group, or a propyl group.

As described above, at least one of $R^7$ to $R^{18}$ may be an electron donating group, and the electron donating group may be for example a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof.

For example, at least one of $R^7$ to $R^{18}$ may be a C1 to C10 alkyl group, a C3 to C12 cycloalkyl group, a C6 to C12 aryl group, a C1 to C10 alkoxy group, —$NR^aR^b$, —$NHCOR^c$, —$OCOR^d$, a hydroxy group, or a combination thereof and may be, for example each independently a methyl group, an ethyl group, a propyl group, an isopropyl group, a butyl group, a pentyl group, a cyclopentyl group, a cyclohexyl group, a phenyl group, a biphenyl group, a naphthyl group, a methoxy group, an ethoxy group, a propoxy group, or a butoxy group.

For example, at least two of $R^7$ to $R^{18}$ may be a C1 to C10 alkyl group, a C3 to C12 cycloalkyl group, a C6 to C12 aryl group, a C1 to C10 alkoxy group, —$NR^aR^b$, —$NHCOR^c$, —$OCOR^d$, a hydroxy group, or a combination thereof, and may be, for example each independently a methyl group, an ethyl group, a propyl group, an isopropyl group, a butyl group, a pentyl group, a cyclopentyl group, a cyclohexyl group, a phenyl group, a biphenyl group, a naphthyl group, a methoxy group, an ethoxy group, a propoxy group, or a butoxy group.

For example, at least one of $R^7$ to $R^{12}$ and at least one of $R^{13}$ to $R^{18}$ may be a C1 to C10 alkyl group, a C3 to C12 cycloalkyl group, a C6 to C12 aryl group, a C1 to C10 alkoxy group, —$NR^aR^b$, —$NHCOR^c$, —$OCOR^d$, a hydroxy group, or a combination thereof, and may be, for example each independently a methyl group, an ethyl group, a propyl group, an isopropyl group, a butyl group, a pentyl group, a cyclopentyl group, a cyclohexyl group, a phenyl group, a biphenyl group, a naphthyl group, a methoxy group, an ethoxy group, a propoxy group, or a butoxy group.

For example, at least one of $R^8$, $R^{10}$, $R^{14}$, and $R^{16}$ may be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof, and may be, for example each independently a methyl group, an ethyl group, a propyl group, an isopropyl group, a butyl group, a pentyl group, a cyclopentyl group, a cyclohexyl group, a phenyl group, a biphenyl group, a naphthyl group, a methoxy group, an ethoxy group, a propoxy group, or a butoxy group.

For example, one of $R^8$ and $R^{19}$ and one of $R^{14}$ and $R^{16}$ may be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof, and may be, for example each independently a methyl group, an ethyl group, a propyl group, an isopropyl group, a butyl group, a pentyl group, a cyclopentyl group, a cyclohexyl group, a phenyl group, a biphenyl group, a naphthyl group, a methoxy group, an ethoxy group, a propoxy group, or a butoxy group.

For example, $R^8$ and $R^{14}$ may each independently be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof, and may be, for example each independently a methyl group, an ethyl group, a propyl group, an isopropyl group, a butyl group, a pentyl group, a cyclopentyl group, a cyclohexyl group, a phenyl group, a biphenyl group, a naphthyl group, a methoxy group, an ethoxy group, a propoxy group, or a butoxy group. For example, each of $R^7$, $R^9$ to $R^{13}$, and $R^{15}$ to $R^{18}$ may be hydrogen.

For example, $R^{19}$ and $R^{16}$ may each independently be a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof, and may be, for example each independently a methyl group, an ethyl group, a propyl group, an isopropyl group, a butyl group, a pentyl group, a cyclopentyl group, a cyclohexyl group, a phenyl group, a biphenyl group, a naphthyl group, a methoxy group, an ethoxy group, a propoxy group, or a butoxy group. For example, each of $R^7$ to $R^9$, $R^{11}$ to $R^{15}$, and $R^{17}$ may be hydrogen.

For example, $R^{19}$ to $R^{27}$ may each independently be hydrogen, a substituted or unsubstituted C1 to C20 alkyl group, a substituted or unsubstituted C1 to C20 alkoxy group, or a hydroxyl group.

For example, two of $R^{19}$ to $R^{27}$ may be linked with each other to form a ring. For example, $R^{19}$ and $R^{21}$, $R^{20}$ and $R^{22}$, $R^{21}$ and $R^{23}$, $R^{22}$ and $R^{24}$, $R^{23}$ and $R^{25}$, $R^{24}$ and $R^{26}$ and/or $R^{25}$ and $R^{27}$ may be linked with each other to form a ring. Herein, the ring may be a C3 to C10 aliphatic ring or a C6 to C12 aromatic ring, for example cyclopentene, cyclohexene, or benzene.

For example, the compound may be for example represented by Chemical Formula 1A or 1B.

[Chemical Formula 1A]

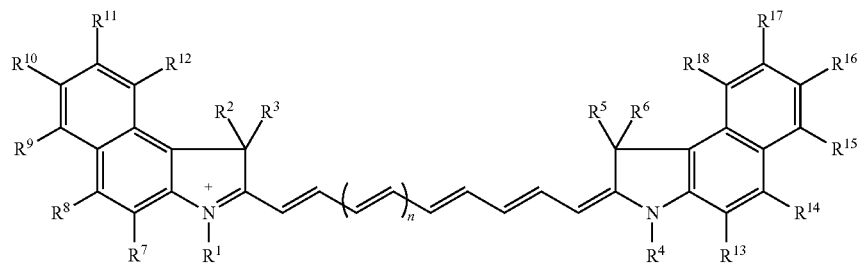

[Chemical Formula 1B]

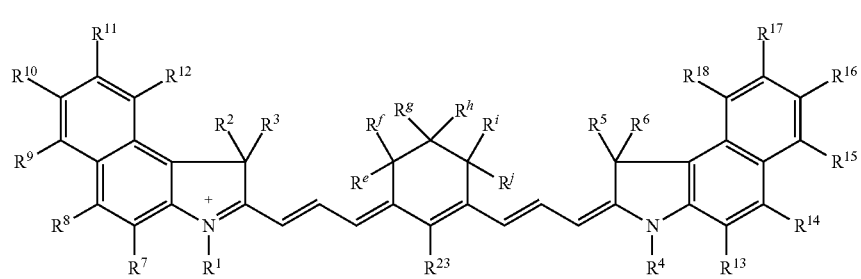

In Chemical Formula 1A or 1B, $R^1$ to $R^{18}$, $R^{23}$, and n are the same as described above, $R^e$ to $R^j$ are each independently hydrogen, a substituted or unsubstituted C1 to C20 alkyl group, a substituted or unsubstituted C6 to C20 aryl group, or a combination thereof.

For example, the compound represented by Chemical Formula 1A may be represented by Chemical Formula 1A-1 or 1A-2.

[Chemical Formula 1A-1]

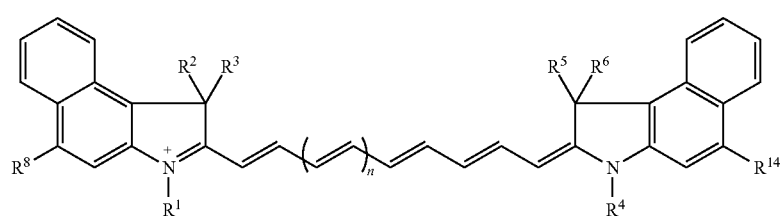

[Chemical Formula 1A-2]

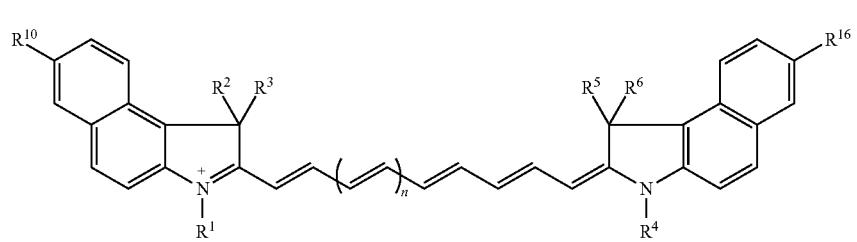

In Chemical Formulae 1A-1 and 1A-2, $R^1$ to $R^6$, $R^8$, $R^{10}$, $R^{14}$, $R^{16}$, and n are the same as described above.

For example, the compound represented by Chemical Formula 1B may be represented by Chemical Formula 1B-1 or 1B-2.

[Chemical Formula 1B-1]

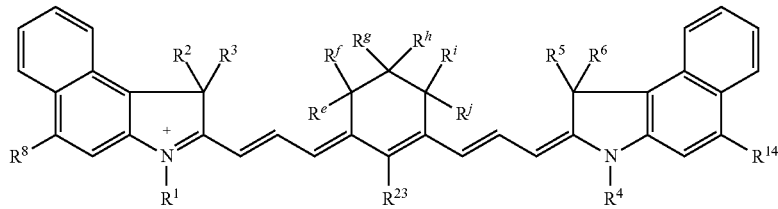

[Chemical Formula 1B-2]

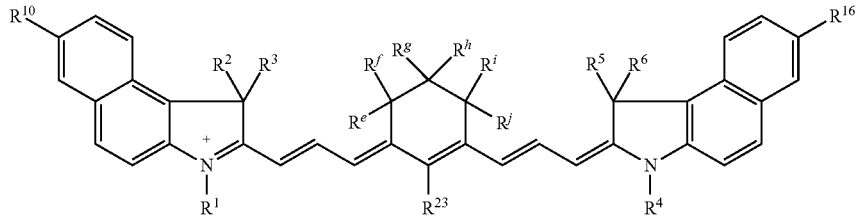

In Chemical Formulae 1B-1 or 1B-2, $R^1$ to $R^6$, $R^8$, $R^{10}$, $R^{14}$, $R^{16}$, and $R^e$ to $R^j$ are the same as described above.

The compound represented by Chemical Formulae 1A-1, 1A-2, 1B-1, or 1B-2 has the benzoindole moiety substituted with the electron-donating group in a desired (and/or alternatively predetermined) position and thus may much further absorb light of a long wavelength in a near-infrared wavelength region, and a maximum absorption wavelength ($\lambda_{max}$) thereof may be much further exhibited in the long wavelength region.

The nitrogen (N) in the indole ring of the compound may be cationic, and the compound may include an anion that is paired with the cation. The anion may be for example $F^-$, $Cl^-$, $Br^-$, $Cl^-$, $PF_6^-$, or $SO_3^-$, but is not limited thereto.

As described above, the aforementioned compound may exhibit high light absorption characteristics in the near-infrared wavelength region, and thus may be applied in various fields where light absorption characteristics of the near-infrared wavelength region are desired (and/or required).

For example, the compound may be applied to an optical filter that requires light absorption characteristics of the near-infrared wavelength region. The optical filter may be for example a near-infrared absorption filter.

The optical filter may be configured to transmit light in a visible region and may be configured to selectively absorb at least a portion of light in the near-infrared region. The visible region may be for example a wavelength region of greater than or equal to about 400 nm and less than about 700 nm and the near-infrared region of light may be for example a wavelength region of about 700 nm to about 1200 nm. For example, the optical filter may absorb light in a wavelength region of about 850 nm to about 1100 nm, for example about 870 nm to about 1050 nm, about 880 nm to about 1000 nm, about 890 nm to about 990 nm, about 900 nm to about 990 nm, about 910 nm to about 990 nm, or about 920 nm to about 990 nm.

FIG. 1 is a cross-sectional view showing an optical filter according to an embodiment.

The optical filter 10 includes a substrate 11 and a light absorbing layer 12.

The substrate 11 may be a transparent substrate or a transparent thin film. The substrate 11 may include for example an organic material, an inorganic material, an organic/inorganic material, or a combination thereof, for example oxide, nitride, sulfide, fluoride, a polymer, or a combination thereof, for example glass, silicon oxide, aluminum oxide, magnesium fluoride, polystyrene, polyacrylate, polymethylmethacrylate, polyethyleneterephthalate, polyethylenenaphthalate, triacetyl cellulose, polycarbonate, a cycloolefin polymer, polyimide, polyamideimide, or a combination thereof, but is not limited thereto. The substrate 11 may be omitted as needed.

The light absorbing layer 12 may be formed from a composition including the aforementioned compound and may include the composition and/or a cured product of the composition.

The composition may also include one or more other light absorbing materials besides the aforementioned compound as the near-infrared light absorbing material. The additionally added light absorbing material may include for example a quinoid metal complex compound, a phthalocyanine compound, a merocyanine compound, a naphthalocyanine compound, an immonium compound, a diimmonium compound, a triarylmethane compound, a dipyrromethene compound, an anthraquinone compound, a diquinone compound, a naphthoquinone compound, a squarylium compound, a rylene compound, a perylene compound, a pyrylium compound, a squaraine compound, a thiopyrylium compound, a diketopyrrolopyrrole) compound, a boron-dipyrromethene compound, a nickel-dithiol complex compound, a croconium compound, a derivative thereof, or a combination thereof, but is not limited thereto.

The composition may optionally further include a binder. The binder may be an organic binder, an inorganic binder, an organic/inorganic binder, or a combination thereof, and is not particularly limited as long as it is a material capable of mixing with the aforementioned compound or dispersing the aforementioned compound, or binding the aforementioned compound. The binder may be a curable binder, for example a thermally curable binder, a photo-curable binder, or a combination thereof. The binder may be for example a (meth)acryl((meth)acryl) binder, methyl cellulose, ethyl cellulose, hydroxypropyl methyl cellulose (HPMC), hydroxylpropyl cellulose (HPC), xanthan gum, polyvinyl alcohol (PVA), polyvinyl pyrrolidone (PVP), a cyclic olefin polymer (COP), carboxy methyl cellulose, hydroxyl ethyl cellulose, silicone, organic-inorganic hybrid materials, a copolymer thereof, or a combination thereof, but is not limited thereto.

The aforementioned compound may be for example included in an amount of about 0.01 to about 50 parts by weight, about 0.01 to about 30 parts by weight, about 0.01 to about 20 parts by weight, about 0.01 to about 15 parts by weight, or about 0.01 to about 10 parts by weight based on 100 parts by weight of the binder.

In addition to the aforementioned compound and binders, the composition may optionally further include a solvent. The solvent is not particularly limited as long as it may dissolve and/or disperse the aforementioned compound and binder. The solvent may be for example at least one of water; an alcohol based solvent such as methanol, ethanol, n-propylalcohol, isopropylalcohol, n-butanol, isobutanol, t-butanol, propylene glycol, propylene glycolmethylether, ethylene glycol, and the like; an aliphatic hydrocarbon solvent such as hexane, heptane, and the like; an aromatic or heteroaromatic hydrocarbon solvent such as toluene, pyridine, quinoline, anisole, mesitylene, xylene and the like; a ketone based solvent such as methyl isobutyl ketone, 1-methyl-2-pyrrolidinone (NMP), cyclohexanone, acetone, and the like; an ether based solvent such as tetrahydrofuran, isopropyl ether, and the like; an acetate based solvent such as ethyl acetate, butyl acetate, propylene glycol methyl ether acetate and the like; an amide based solvent such as dimethylacetamide, dimethyl formamide (DMF), and the like; a nitrile based solvent such as acetonitrile, benzonitrile, and the like; and a mixture of the foregoing solvents, but is not limited thereto.

The composition may be coated and dried on substrate 11 and optionally cured. The coating may be for example a spin coating, a slit coating, a bar coating, a blade coating, a slot die coating, and/or an inkjet coating. The drying may be for example performed by natural drying, hot air drying, and/or a heat treatment at a higher temperature than the boiling point of the aforementioned solvent. The curing may be thermal curing, photo curing, or a combination thereof.

The optical filter 10 may be configured to effectively transmit light in a visible wavelength region but effectively absorb light in a near-infrared wavelength region and thus may be effectively applied as an optical filter configured to block light in the near-infrared wavelength region in a sensor sensing light like an image sensor. In addition, the optical filter includes the aforementioned compound and exhibits sufficient light absorption characteristics with a thin thickness and accordingly, may be integrated in the sensor like the image sensor and thus realize an internal optical filter.

The optical filter 10 may be usefully applied to an electronic device including for example an image sensor, a camera module, and the like. The electronic device may be a digital camera, a camcorder, a monitoring camera such as CCTV, an in-car camera, a medical camera, a cell phone having a built-in or external camera, a computer having a built-in or external camera, a laptop computer having a built-in or external camera, and the like but is not limited thereto.

Hereinafter, an embodiment of a camera module having an optical filter will be described.

Figure 2:
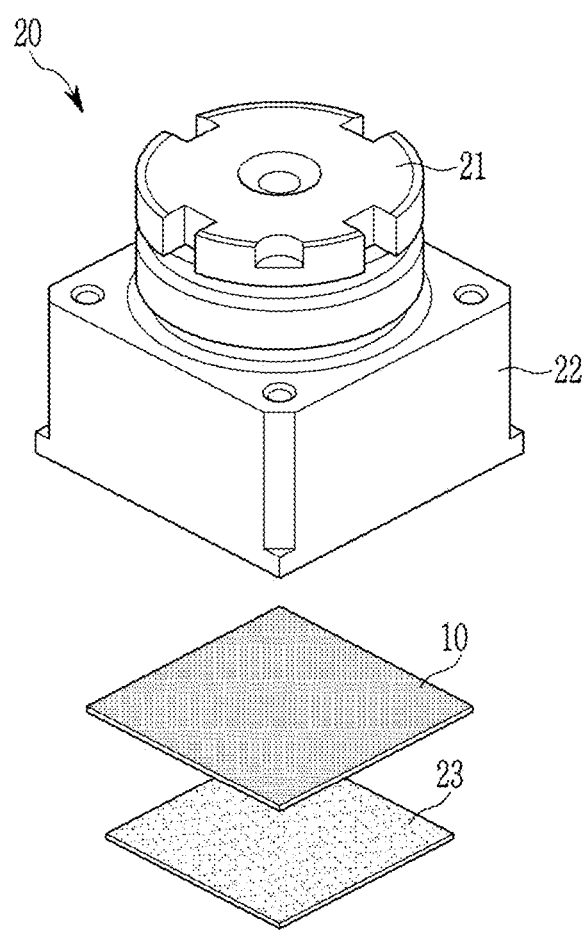
FIG. 2 is a schematic view showing a camera module according to an embodiment.

FIG. 2 is a schematic view showing a camera module according to an embodiment.

Referring to FIG. 2, a camera module 20 includes a lens barrel 21, a housing 22, an optical filter 10, and an image sensor 23.

The lens barrel 21 includes at least one lens imaging a subject, and the lens may be disposed along an optical axis direction. Herein, the optical axis direction may be a vertical direction of the lens barrel 21. The lens barrel 21 is internally housed in the housing 22 and united with the housing 22. The lens barrel 21 may be moved in optical axis direction inside the housing 22 for autofocusing.

The housing 22 supports and houses the lens barrel 21 and may be open in the optical axis direction. Accordingly, incident light from one surface of the housing 22 may reach the image sensor 23 through the lens barrel 21 and the optical filter 10.

The housing 22 may be equipped with an actuator for moving the lens barrel 21 in the optical axis direction. The actuator may include a voice coil motor (VCM) including a magnet and a coil. However, various methods such as a mechanical driving system or a piezoelectric driving system using a piezoelectric device other than the actuator may be adopted.

The optical filter 10 is the same as described above.

The image sensor 23 may concentrate an image of a subject and thus store it as data, and the stored data may be displayed as an image through a display media.

The image sensor 23 may be mounted in a substrate (not shown) and electrically connected to the substrate. The substrate may be, for example, a printed circuit board (PCB) or electrically connected to a printed circuit board, and the printed circuit may be, for example, a flexible printed circuit (FPCB).

The image sensor 23 concentrates light passing the lens barrel 21 and the optical filter 10 and generates a video signal and may be a complementary metal-oxide semiconductor (CMOS) image sensor and/or a charge coupled device (CCD) image sensor.

In the above description, the camera module including the image sensor 23 and the optical filter 10 is separately provided. However, the optical filter 10 may be included in the image sensor 23 as an optical filter-integrated image sensor.

Hereinafter, an example of an optical filter-integrated image sensor will be described with reference to a drawing. As an example of an image sensor, a CMOS image sensor is described.

Figure 3:
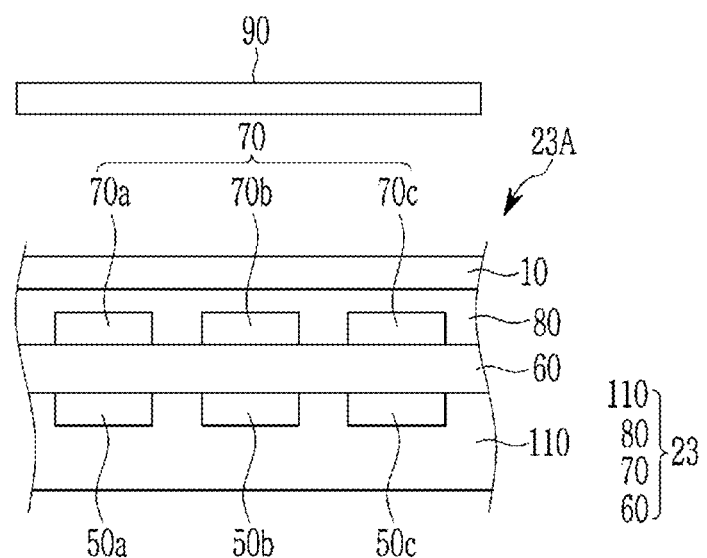
FIG. 3 is a cross-sectional view showing an image sensor according to an embodiment.

FIG. 3 is a cross-sectional view showing an image sensor according to an embodiment.

An image sensor 23A according to an embodiment includes a semiconductor substrate 110, a lower insulation layer 60, a color filter layer 70, an upper insulation layer 80, and an optical filter 10.

The semiconductor substrate 110 may be a silicon substrate, and is integrated with the photo-sensing devices 50a, 50b, and 50c, and transmission transistor (not shown). The photo-sensing devices 50a, 50b, and 50c may be photodiodes. For example, the photo-sensing device 50a may be a blue photo-sensing device 50a configured to sense light in a blue wavelength region which passes a blue filter 70a described later, the photo-sensing device 50b may be a green photo-sensing device 50b configured to sense light in a green wavelength region which passes a green filter 70b described later, and the photo-sensing device 50c may be a red photo-sensing device 50c configured to sense light in a red wavelength region passes a red filter 70c described later. The photo-sensing devices 50a, 50b, and 50c and the transmission transistor may be integrated in each pixel. The photo-sensing devices 50a, 50b, and 50c sense light and the sensed information may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing devices 50a, 50b, and 50c.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF.

The color filter layer 70 is formed on the lower insulation layer 60. The color filter layer 70 includes a blue filter 70a formed in a blue pixel, a green filter 70b formed in a green pixel, and a red filter 70c formed in a red pixel. However, the present disclosure is not limited thereto, but at least one of the blue filter 70a, the green filter 70b, and the red filter 70c may be replaced by a yellow filter, a cyan filter, or a magenta filter.

An upper insulation layer 80 is formed on the color filter layer 70. The upper insulation layer 80 may provide a flat surface by reducing stepped portions formed by the color filter layer 70. The upper insulation layer 80 may be made of an inorganic insulating material such as silicon oxide and/or silicon nitride or an organic insulating material. The upper insulation layer 80 may be omitted as needed.

The optical filter 10 is formed on the upper insulation layer 80. Herein, a structure where the optical filter 10 is disposed on the color filter layer 70 is described, but the optical filter 10 may be disposed under the color filter layer 70. The optical filter 10 may include the aforementioned compound and/or a cured product thereof and may effectively absorb light in the near-infrared wavelength region. In the case that the upper insulation layer 80 is the same as the substrate 11 of the optical filter 10, either the upper insulation layer 80 or the substrate 11 may be omitted. Details of the optical filter 10 are the same as described above.

Focusing lens (not shown) may be further formed on the optical filter 10. However, the present disclosure is not limited to this, and the optical filter 10 may be disposed on the focusing lens. The focusing lens may control a direction of incident light and gather the light in one region. The focusing lens may have a shape of, for example, a cylinder or a hemisphere, but is not limited thereto.

A dual bandpass filter 90 may be disposed on the focusing lens. The dual bandpass filter 90 may selectively transmit light in at least two wavelength regions of incident light and may for example selectively transmit light in a visible wavelength region and in a portion of the near-infrared wavelength region.

As described above, the optical filter 10 may effectively transmit light in the visible region and effectively absorb and block light in the other regions like the near-infrared wavelength region except for the visible region and thus transfer pure light in the visible region to the image sensor and accordingly, reduce or prevent a crosstalk generated when a signal by light of the visible region is crossed and mingled with another signal by light of a non-visible region and particularly, the near-infrared wavelength region.

Particularly, the optical filter 10 has a sufficiently thin thickness and thus may be realized into an optical filter-integrated image sensor equipped inside the image sensor 23A and accordingly, may realize thinness of an image sensor, a camera module, and an electronic device equipped therewith.

Figure 4:
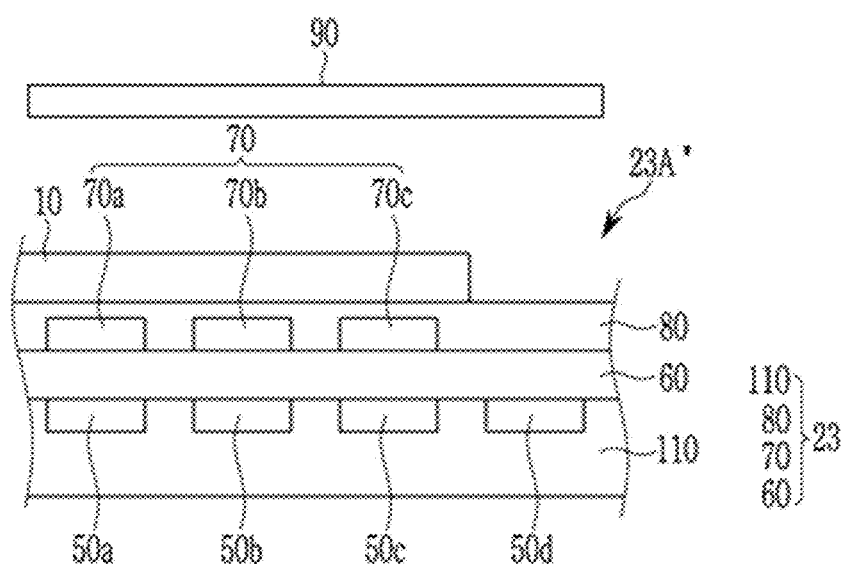
FIG. 4 is a cross-sectional view illustrating an image sensor according to another embodiment.

FIG. 4 is a cross-sectional view illustrating an image sensor according to another embodiment.

The image sensor 23A' according to the present embodiment may include the semiconductor substrate 110, the lower insulation layer 60, the color filter layer 70, the upper insulation layer 80, and the optical filter 10, like the aforementioned embodiment.

However, the image sensor 23A' according to the present embodiment further includes a photo-sensing device 50d for sensing light belonging to the infrared wavelength region unlike the aforementioned embodiment. The color filter layer 70 may include a transparent filter or a white color filter 70d at the position corresponding to the photo-sensing device 50d or just have an empty space without a particular filter.

The optical filter 10 may be disposed either on or under the blue filter 70a, the green filter 70b, and the red filter 70c but neither on nor under the transparent filter or the white color filter 70d.

The dual bandpass filter 90 may be configured to for example selectively transmit light in a visible wavelength region and in a portion of the near-infrared wavelength region.

For example, the photo-sensing device 50d may be used as an auxiliary device to improve sensitivity of the image sensor under a low-illumination environment.

For example, the photo-sensing device 50d may be used as an infrared sensor configured to sense light in a near-infrared wavelength region. The infrared sensor may be for example a biometric sensor, for example an iris sensor, a depth sensor, a fingerprint sensor, a blood vessel distribution sensor, but is not limited thereto.

The aforementioned image sensor and/or camera module may be applicable to various electronic devices, for example a digital camera, a camcorder, a monitoring camera such as CCTV, an in-car camera, a medical camera, a cell phone having a built-in or external camera, a computer having a built-in or external camera, a laptop computer having a built-in or external camera, and the like but is not limited thereto.

Hereinafter, the embodiments are illustrated in more detail with reference to examples. However, these examples are non-limiting, and the present scope is not limited thereto.

DFT Simulation

Light absorption characteristics of the compounds represented by Chemical Formulae 1A-1, 1B-1, and 1B-2 are calculated through a DFT (density functional theory) simulation by using a software of Gaussian 16 (Expanding the limits of computational chemistry), and the calculated results are calibrated with reference to Dyes and Pigments 2015,121,238 to confirm maximum absorption wavelengths ($\lambda_{max}$).

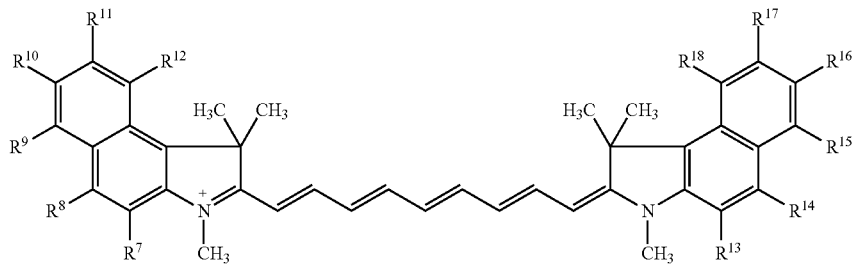

[Chemical Formula 1A-a]

TABLE 1

| No. | $R^7, R^{13}$ | $R^8, R^{14}$ | $R^9, R^{15}$ | $R^{10}, R^{16}$ | $R^{11}, R^{17}$ | $R^{12}, R^{18}$ | $\lambda_{max}$ (nm) |
|---|---|---|---|---|---|---|---|
| 1-1 | OCH$_3$ | H | H | H | H | H | 901 |
| 1-2 | H | OCH$_3$ | H | H | H | H | 909 |
| 1-3 | H | H | H | OCH$_3$ | H | H | 913 |
| 1-4 | H | CH(CH$_3$)$_2$ | H | H | H | H | 901 |
| 1-5 | H | H | H | CH(CH$_3$)$_2$ | H | H | 904 |
| 1-6 | H | H | H | H | CH(CH$_3$)$_2$ | H | 900 |
| 1-7 | H | CH$_3$ | H | H | H | H | 900 |
| 1-8 | H | H | H | CH$_3$ | H | H | 901 |
| Reference Example1 | H | H | H | H | H | H | 894 |

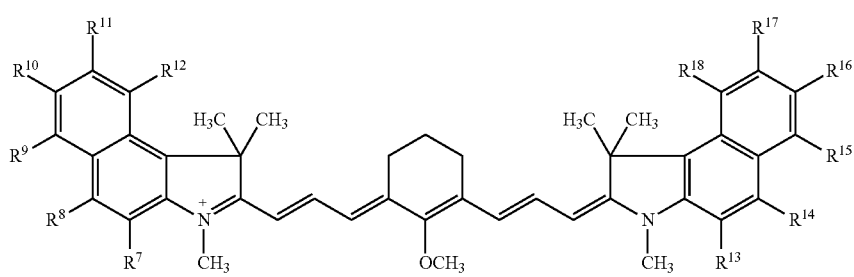

[Chemical Formula 1B-a]

TABLE 2

| No. | $R^7, R^{13}$ | $R^8, R^{14}$ | $R^9, R^{15}$ | $R^{10}, R^{16}$ | $R^{11}, R^{17}$ | $R^{12}, R^{18}$ | $\lambda_{max}$ (nm) |
|---|---|---|---|---|---|---|---|
| 2-1 | OCH$_3$ | H | H | H | H | H | 940 |
| 2-2 | H | OCH$_3$ | H | H | H | H | 946 |
| 2-3 | H | H | H | OCH$_3$ | H | H | 950 |
| 2-4 | H | CH(CH$_3$)$_2$ | H | H | H | H | 940 |
| 2-5 | H | H | H | CH(CH$_3$)$_2$ | H | H | 943 |
| 2-6 | H | H | H | H | CH(CH$_3$)$_2$ | H | 939 |
| 2-7 | H | CH$_3$ | H | H | H | H | 939 |
| 2-8 | H | H | H | CH$_3$ | H | H | 940 |
| Reference Example2 | H | H | H | H | H | H | 933 |
| Reference Example3 | H | CN | H | H | H | H | 929 |
| Reference Example4 | H | CO$_2$CH$_3$ | H | H | H | H | 933 |

** CN, CO$_2$CH$_3$: electron withdrawing group

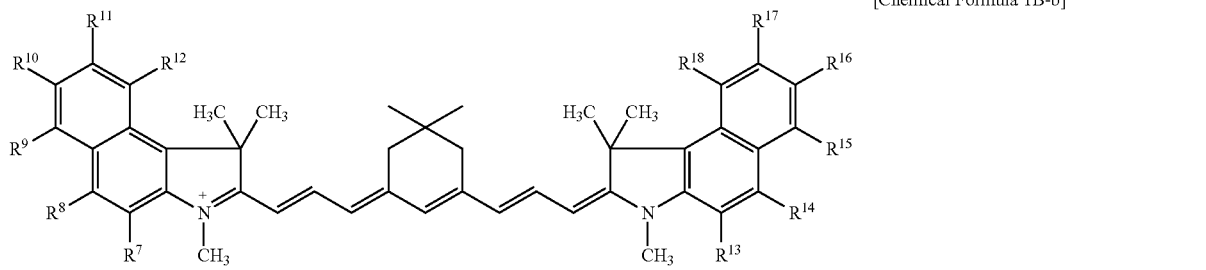

[Chemical Formula 1B-b]

TABLE 3

| No. | $R^7, R^{13}$ | $R^8, R^{14}$ | $R^9, R^{15}$ | $R^{10}, R^{16}$ | $R^{11}, R^{17}$ | $R^{12}, R^{18}$ | $\lambda_{max}$ (nm) |
|---|---|---|---|---|---|---|---|
| 3-1 | H | OCH$_3$ | H | H | H | H | 923 |
| 3-2 | H | H | H | OCH$_3$ | H | H | 927 |
| 3-3 | H | CH(CH$_3$)$_2$ | H | H | H | H | 917 |
| 3-4 | H | H | H | CH(CH$_3$)$_2$ | H | H | 919 |
| 3-5 | H | H | H | CH$_3$ | H | H | 916 |
| Reference Example 5 | H | H | H | H | H | H | 910 |

Referring to Tables 1, 2, and 3, a maximum absorption wavelength ($\lambda_{max}$) of the compound of Chemical Formula 1A-1, 1B-1, or 1B-2 having a benzoindole moiety substituted with an electron donating group is greater than or equal to about 5 nm shifted toward a long wavelength region compared with that of a comparative compound having an unsubstituted benzoindole moiety.

While this disclosure has been described in connection with what is presently considered to be practical example embodiments, it is to be understood that inventive concepts not limited to the disclosed embodiments. On the contrary, inventive concepts are intended to cover various modifications and equivalent arrangements included within the spirit and scope of the appended claims.

What is claimed is:

1. A compound represented by Chemical Formula 1A or 1B:

[Chemical Formula 1A]

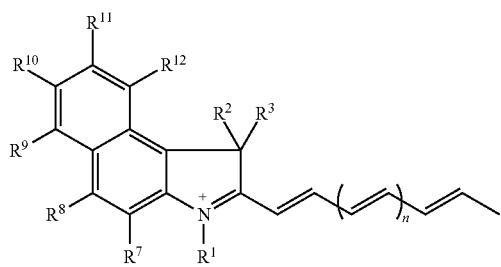

-continued

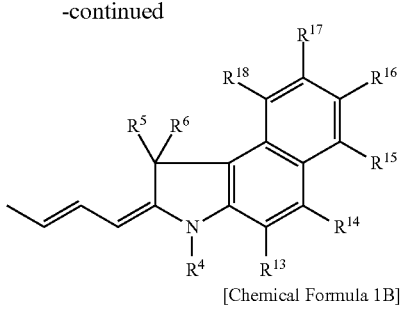

[Chemical Formula 1B]

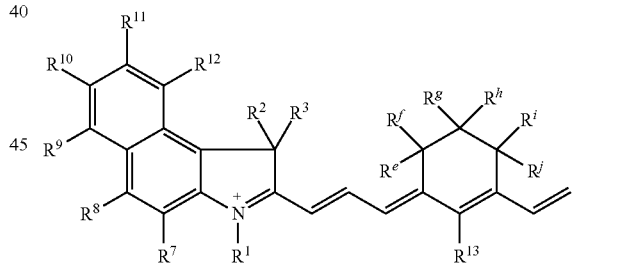

wherein, in Chemical Formulas 1A and 1B, $R^1$ to $R^6$ are each independently hydrogen or a C1 to C5 alkyl group, wherein in Chemical Formula 1A, $R^7$ to $R^{18}$ are each independently hydrogen, a substituted or unsubstituted C1 to C20 alkyl group, a substituted or unsubstituted C3 to C20 cycloalkyl group, a substituted or unsubstituted C6 to C20 aryl group, a substituted or unsubstituted C3 to C20 heterocyclic group, a substituted or unsubstituted C1 to C20 alkoxy group, —NR$^a$R$^b$, —NHCOR$^c$, —OCOR$^d$, a hydroxy group, a halogen, a cyano group, or a combination thereof, wherein, in Chemical Formula 1A, at least one of R$^7$ to R$^{18}$ is a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —NR$^a$R$^b$, —NHCOR$^c$, —OCOR$^d$, a hydroxy group, or a combination thereof, wherein, in Chemical Formula 1A, R$^a$ to R$^d$ are each independently hydrogen, a substituted or unsubstituted C1 to C20 alkyl group, a substituted or unsubstituted C6 to C20 aryl group, or a combination thereof, wherein, in Chemical Formula 1A, n is 1 or 2, wherein, in Chemical Formula 1B, R$^7$ to R$^{18}$ and R$^{23}$ are each independently hydrogen, a substituted or unsubstituted C1 to C20 alkyl group, a substituted or unsubstituted C3 to C20 cycloalkyl group, a substituted or unsubstituted C6 to C20 aryl group, a substituted or unsubstituted C3 to C20 heterocyclic group, a substituted or unsubstituted C1 to C20 alkoxy group, —NR$^a$R$^b$, —NHCOR$^c$, —OCOR$^d$, a hydroxy group, a halogen, a cyano group, or a combination thereof, wherein, in Chemical Formula 1B, at least one of R$^7$ to R$^{18}$ is a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —NR$^a$R$^b$, —NHCOR$^c$, —OCOR$^d$, a hydroxy group, or a combination thereof, and wherein, in Chemical Formula 1B, R$^a$ to R$^j$ are each independently hydrogen, a substituted or unsubstituted C1 to C20 alkyl group, a substituted or unsubstituted C6 to C20 aryl group, or a combination thereof.

2. The compound of claim 1, wherein the compound is represented by Chemical Formula 1A.

3. The compound of claim 1, wherein
in Chemical Formulas 1A and 1B,
at least one of R$^8$, R$^{10}$, R$^{14}$, and R$^{16}$ is a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —NR$^a$R$^b$, —NHCOR$^c$, —OCOR$^d$, a hydroxy group, or a combination thereof, and wherein R$^a$ to R$^d$ are each independently hydrogen, a substituted or unsubstituted C1 to C20 alkyl group, a substituted or unsubstituted C6 to C20 aryl group, or a combination thereof.

4. The compound of claim 3, wherein
in Chemical Formulas 1A and 1B,
R$^8$ and R$^{14}$ are each independently a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —NR$^a$R$^b$, —NHCOR$^c$, —OCOR$^d$, a hydroxy group, or a combination thereof, and wherein R$^a$ to R$^d$ are each independently hydrogen, a substituted or unsubstituted C1 to C20 alkyl group, a substituted or unsubstituted C6 to C20 aryl group, or a combination thereof.

5. The compound of claim 3, wherein
in Chemical Formulas 1A and 1B,
R$^{10}$ and R$^{16}$ are each independently a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —NR$^a$R$^b$, —NHCOR$^c$, —OCOR$^d$, a hydroxy group, or a combination thereof, and wherein R$^a$ to R$^d$ are each independently hydrogen, a substituted or unsubstituted C1 to C20 alkyl group, a substituted or unsubstituted C6 to C20 aryl group, or a combination thereof.

6. The compound of claim 1, wherein R$^1$ to R$^6$ are each independently a methyl group, an ethyl group, or a propyl group.

7. The compound of claim 1, wherein the compound is represented by Chemical Formula 1B.

8. The compound of claim 2, wherein
at least one of R$^8$, R$^{10}$, R$^{14}$, and R$^{16}$ is a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —NR$^a$R$^b$, —NHCOR$^c$, —OCOR$^d$, a hydroxy group, or a combination thereof, and wherein R$^a$ to R$^d$ are each independently hydrogen, a substituted or unsubstituted C1 to C20 alkyl group, a substituted or unsubstituted C6 to C20 aryl group, or a combination thereof.

9. The compound of claim 1, wherein the compound is represented by one of Chemical Formulae 1A-1, 1A-2, 1B-1, and 1B-2:

[Chemical Formula 1A-1]

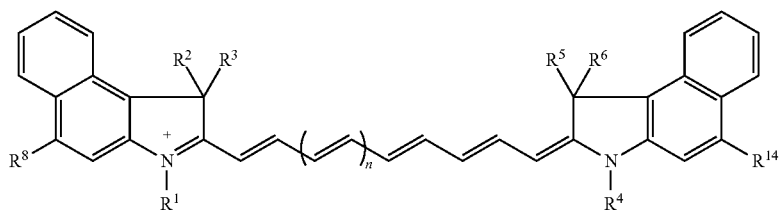

-continued

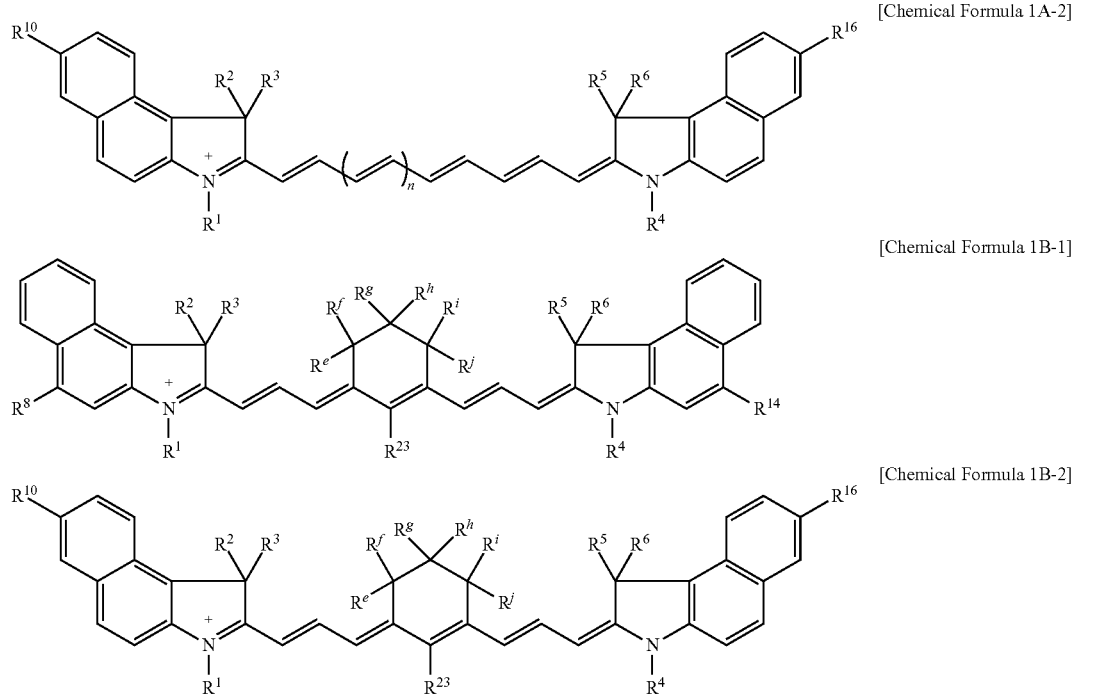

[Chemical Formula 1A-2]

[Chemical Formula 1B-1]

[Chemical Formula 1B-2]

wherein in Chemical Formulae 1A-1, 1A-2, 1B-1, and 1B-2, $R^1$ to $R^6$ are each independently hydrogen or a C1 to C5 alkyl group, $R^8$, $R^{10}$, $R^{14}$, and $R^{16}$ are each independently a substituted or unsubstituted C1 to C20 alkyl group, a substituted or unsubstituted C3 to C20 cycloalkyl group, a substituted or unsubstituted C6 to C20 aryl group, a substituted or unsubstituted C1 to C20 alkoxy group, —$NR^aR^b$, —$NHCOR^c$, —$OCOR^d$, a hydroxy group, or a combination thereof, $R^a$ to $R^d$ are each independently hydrogen, a substituted or unsubstituted C1 to C20 alkyl group, a substituted or unsubstituted C6 to C20 aryl group, or a combination thereof, wherein, in Chemical Formulae 1A-1 and 1A-2, n is 1 or 2, and wherein in Chemical Formulae 1B-1 and 1B-2, $R^e$ to $R^j$ are each independently hydrogen, a substituted or unsubstituted C1 to C20 alkyl group, a substituted or unsubstituted C6 to C20 aryl group, or a combination thereof.

10. An optical filter comprising:
the compound of claim 1 or a cured product thereof.

11. An image sensor comprising:
a semiconductor substrate, and
an optical filter on the semiconductor substrate, the optical filter configured to absorb at least a portion of light in a near-infrared wavelength region,
wherein the optical filter includes the compound of claim 1 or a cured product thereof.

12. The image sensor of claim 11, wherein the semiconductor substrate includes a plurality of photodiodes.

13. The image sensor of claim 11, further comprising:
a color filter on the semiconductor substrate and on or under the optical filter.

14. The image sensor of claim 11, further comprising:
a dual band-pass filter configured to transmit all of a visible wavelength region and a portion of the near-infrared wavelength region.

15. A camera module comprising:
the optical filter of claim 10.

16. A camera module comprising:
the image sensor of claim 11.

17. An electronic device comprising:
the optical filter of claim 10.

18. An electronic device comprising:
the image sensor of claim 11.

19. An electronic device comprising:
the camera module of claim 15.

20. An electronic device comprising:
the camera module of claim 16.

* * * * *